United States Patent
Ye et al.

(10) Patent No.: US 12,392,748 B2
(45) Date of Patent: Aug. 19, 2025

(54) METHODS, APPARATUSES, AND SYSTEMS PROVIDING GAS DETECTING APPARATUSES AND SENSING COMPONENTS WITH FILTERING ELEMENTS

(71) Applicant: HONEYWELL INTERNATIONAL INC., Charlotte, NC (US)

(72) Inventors: Yifan Ye, Charlotte, NC (US); Feng Liang, Charlotte, NC (US); Lei Xiao, Charlotte, NC (US); Jiafu Xie, Charlotte, NC (US); Jingmeng Peng, Charlotte, NC (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 461 days.

(21) Appl. No.: 17/819,361

(22) Filed: Aug. 12, 2022

(65) Prior Publication Data

US 2023/0071346 A1 Mar. 9, 2023

(30) Foreign Application Priority Data

Aug. 31, 2021 (CN) .......................... 202111012478.2

(51) Int. Cl.
*G01N 27/404* (2006.01)
*G01N 33/00* (2006.01)

(52) U.S. Cl.
CPC ..... *G01N 27/4045* (2013.01); *G01N 33/0011* (2013.01)

(58) Field of Classification Search
CPC ........... G01N 27/4045; G01N 33/0011; G01N 33/0013; G01N 33/0044; G01N 33/0047
See application file for complete search history.

(56) References Cited

U.S. PATENT DOCUMENTS 5,344,546 A * 9/1994 Kiesele .............. G01N 33/0054
204/415
6,284,545 B1 9/2001 Warburton et al.
(Continued)

FOREIGN PATENT DOCUMENTS

CN 103336041 B 3/2016
DE 10330704 B3 * 7/2003 ........... G01N 27/403
(Continued)

OTHER PUBLICATIONS

EPO machine-generated English language translation of Nauber et al. DE 10330704 B3, patent published Dec. 23, 2004 (Year: 2004).*
(Continued)

*Primary Examiner* — Alexander S Noguerola
(74) *Attorney, Agent, or Firm* — Alston & Bird LLP

(57) ABSTRACT

Methods, apparatuses and systems for providing gas detecting apparatuses (e.g., electrochemical detectors) are disclosed herein. An example gas detecting apparatus may comprise a sensing component comprising: a first sensing electrode configured to generate a first concentration level indication associated with a first portion of a sample gaseous substance disposed within the sensing component; and a second sensing electrode operatively coupled to a filtering element that is configured to absorb at least one substance from the sample gaseous substance, wherein the second sensing electrode is configured to generate a second concentration level indication associated with a second portion of the sample gaseous substance.

16 Claims, 7 Drawing Sheets

(56) References Cited

U.S. PATENT DOCUMENTS

| | | | |
|---|---|---|---|
| 11,761,939 B1* | 9/2023 | Cridge | G01N 33/0062 73/31.02 |
| 2014/0174154 A1 | 6/2014 | Marra et al. | |
| 2017/0276634 A1 | 9/2017 | Saffell et al. | |

FOREIGN PATENT DOCUMENTS

| | | |
|---|---|---|
| JP | 2020-098132 A | 6/2020 |
| WO | 2005/015195 A1 | 2/2005 |

OTHER PUBLICATIONS

Hart et al., "A disposable amperometric gas sensor for sulphur-containing compounds based on a chemically modified screen printed carbon electrode coated with a hydrogel," Analytica Chimica Acta 342 (1997) 199-206 (Year: 1997).*

Salt Lake Metals—Solubility of Silver Compounds in water, 2017, downloaded from https://saltlakemetals.com/solubility_of_silver_compounds/?srsltid=AfmBOorNhU9vcqRUzzcwqN895aPwYDQci9SRJx-AbUFjunBa0tL1jIV6 (Year: 2017).*

Aqion—Solubility Product Constants Ksp at 25° C., 2017, downloaded from https://www.aqion.de/site/16 (Year: 2017).*

EP Office Action Mailed on Dec. 8, 2023 for EP Application No. 22188704, 4 page(s).

European search report Mailed on Feb. 7, 2023 for EP Application No. 22188704.

Hart, J.P. et al., "A disposable amperometric gas sensor for sulphur-containing compounds based on a chemically modified screen printed carbon electrode coated with a hydrogel," Analytica Chimica Acta, 342:199-206, (1997).

* cited by examiner

METHODS, APPARATUSES, AND SYSTEMS PROVIDING GAS DETECTING APPARATUSES AND SENSING COMPONENTS WITH FILTERING ELEMENTS

CROSS-REFERENCE TO RELATED APPLICATIONS

This application claims priority pursuant to 35 U.S.C. 119(a) to Chinese Application No. 202111012478.2, filed Aug. 31, 2021, which application is incorporated herein by reference in its entirety.

BACKGROUND

Gas detecting apparatuses (e.g., electrochemical detectors) may comprise sensing components which may be utilized to detect and/or measure the concentration level of gaseous substances and/or compounds in gaseous substances, including, for example, organic compounds and inorganic compounds. Many gas detecting apparatuses are plagued by technical challenges and limitations.

BRIEF SUMMARY

Various embodiments described herein relate to methods, apparatuses, and systems for providing gas detecting apparatuses.

In accordance with various examples of the present disclosure, a gas detecting apparatus is provided. In some examples, the gas detecting apparatus comprises a sensing component, the sensing component comprising: a first sensing electrode configured to generate a first concentration level indication associated with a first portion of a sample gaseous substance disposed within the sensing component; and a second sensing electrode operatively coupled to a filtering element configured to absorb at least one substance from the sample gaseous substance, wherein the second sensing electrode is configured to generate a second concentration level indication associated with a second portion of the sample gaseous substance.

In accordance with various examples of the present disclosure, a method is provided. In some examples, the method comprises: receiving, by a controller component, a first concentration level indication associated with a first portion of a sample gaseous substance from a first sensing electrode; receiving, by the controller component, a second concentration level indication associated with a second portion of the sample gaseous substance from a second sensing electrode that is operatively coupled to a filtering element; and determining, by the controller component, a target substance concentration level indication based at least in part on the first concentration level indication and the second concentration level indication The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which.

DETAILED DESCRIPTION OF THE INVENTION

Figure 1:
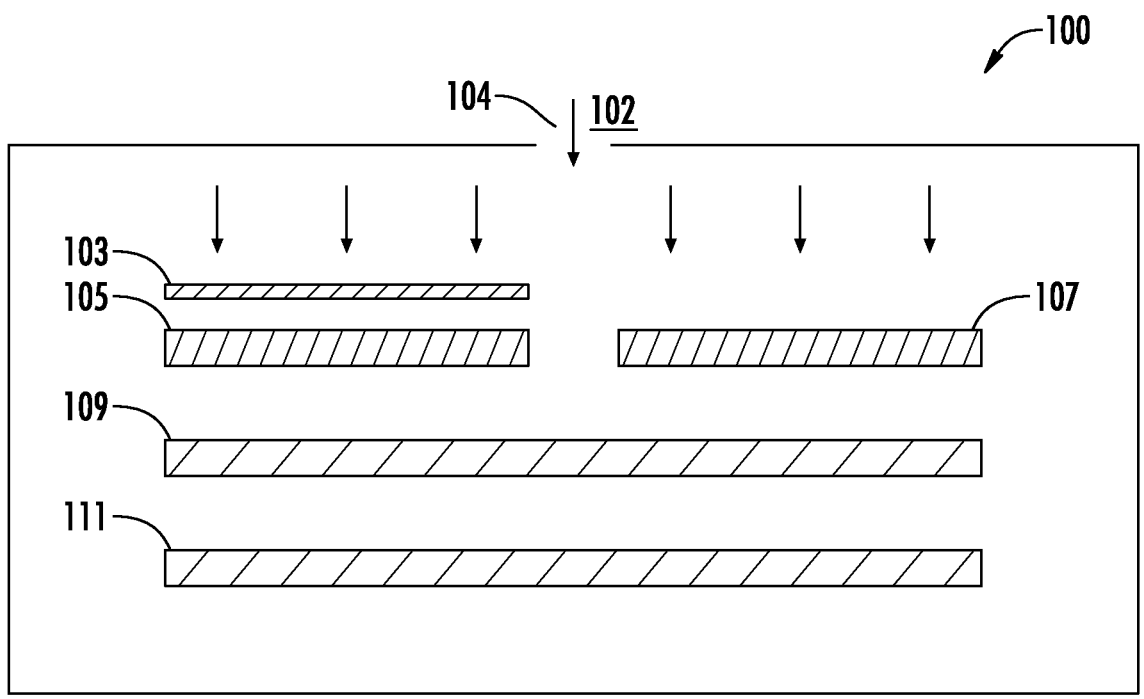
FIG. 1 illustrates an example schematic diagram depicting a portion of an example apparatus in accordance with various embodiments of the present disclosure.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

The components illustrated in the figures represent components that may or may not be present in various embodiments of the present disclosure described herein such that embodiments may include fewer or more components than those shown in the figures while not departing from the scope of the present disclosure. Some components may be omitted from one or more figures or shown in dashed line for visibility of the underlying components.

The phrases "in an example embodiment," "some embodiments," "various embodiments," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that a specific component or feature is not required to be included or to have the characteristic. Such components or features may be optionally included in some embodiments, or may be excluded.

The term "electronically coupled" or "in electronic communication with" in the present disclosure refer to two or more electrical elements (for example, but not limited to, an example processing circuitry, communication module, input/output module memory, humidity sensing component, cooling element, gas detection component) and/or electric circuit(s) being connected through wired means (for example but not limited to, conductive wires or traces) and/or wireless means (for example but not limited to, wireless network, electromagnetic field), such that data and/or information (for example, electronic indications, signals) may be transmitted to and/or received from the electrical elements and/or electric circuit(s) that are electronically coupled.

Various apparatuses (such as, but not limited to, a gas detecting apparatus (e.g., electrochemical detector)) may detect and/or measure a concentration level of one or more target gaseous substances and/or target compounds in a gaseous substance, in some examples, within a specified location or area in order to satisfy regulations and/or meet air quality standards. Target gaseous substances/compounds may include volatile organic compounds (VOCs), toxic gases and the like. By way of example, the presence of malodorous gaseous substances (e.g., sulfide-containing gases such as Hydrogen Sulfide ($H_2S$) and Methanethiol ($CH_3SH$) may be monitored within a particular location (e.g., a factory) in addition to other pollutants such as Carbon Monoxide (CO), Sulphur Dioxide ($SO_2$), Nitrogen Dioxide ($NO_2$) and/or Nitrate ($NO_3$).

In various examples, a gas detecting apparatus may comprise a sensing component that includes a sensing electrode that is configured to detect/measure a concentration of a target gaseous substance. For example, a sample gaseous substance may be directed to flow into a sensing component of a gas detecting apparatus so that it makes contact with (e.g., passes through) the sensing electrode. Many such gas detecting apparatuses (e.g., electrochemical detectors) for detecting the presence of one or more target gaseous substances and/or compounds as described above may present many technical challenges and limitations.

In some embodiments, in monitoring for the presence of a target gaseous substance, other gaseous substances may be present that may react with the same sensing electrode. Accordingly, in some examples, a gas detecting apparatus with a sensing component (e.g., electrochemical detector) comprising a sensing electrode configured to detect/measure the presence of a target gaseous substance may also react to the presence of another gaseous substance. By way of example, $H_2S$ may undergo an oxidizing reaction in response to making contact with a sensing electrode and thus generate a signal indicative of the presence of and/or concentration of $H_2S$. The below formula describes an example of an oxidizing reaction for $H_2S$:

$$H_2S + 4H_2O \rightarrow SO_4^{2-} + 10H^+ + 8e^-$$

Similarly, $CH_3SH$ may also undergo an oxidizing reaction in response to making contact with the sensing electrode and also generate a signal indicative of the presence of and/or concentration of $CH_3SH$. The below formula describes an example of an oxidizing reaction for $CH_3SH$:

$$CH_3SH + H^+ + e^- \rightarrow C_xH_yO_z + SO_4^{2-} + H_2O$$

In the above example, as a result of oxidizing reactions occurring due to the presence of both $H_2S$ and $CH_3SH$, a sensing electrode for detecting only $H_2S$ may generate a false alarm when $CH_3SH$ is present. As such, a gas detecting apparatus may be unable to accurately determine a concentration level of $H_2S$ when $CH_3SH$ is present in a sample gaseous substance. This may result in false positive alarms being generated by the example gas detecting apparatus in some applications. In some examples, this may also lead to inaccurate measurements of concentration(s) of target gaseous substance(s) by an example gas detecting apparatus.

In accordance with various embodiments of the present disclosure, example methods, apparatuses and systems are provided.

In some examples, a gas detecting apparatus is provided. The gas detecting apparatus may comprise a sensing component. In some examples, the sensing component may comprise: a first sensing electrode configured to generate a first concentration level indication associated with a first portion of a sample gaseous substance disposed within the sensing component; and a second sensing electrode operatively coupled to a filtering element configured to absorb at least one substance from the sample gaseous substance, wherein the second sensing electrode is configured to generate a second concentration level indication associated with a second portion of the sample gaseous substance. In some examples, the gas detecting apparatus further comprises a controller component in electronic communication with the sensing component. In some examples, the controller component is configured to: receive the first concentration level indication and the second concentration level indication; and determine a target substance concentration level based at least in part on the first concentration level indication and the second concentration level indication. In some examples, the first sensing electrode and the second sensing electrode are in a coplanar arrangement with respect to one another. In some examples, the filtering element is disposed above the first sensing electrode. In some examples, the sample gaseous substance comprises $H_2S$ and $CH_3SH$, and the at least one substance comprises $H_2S$. In some examples, the first concentration level indication is associated with a concentration of $H_2S$ and $CH_3SH$, and the second concentration level indication is associated with a concentration of $CH_3SH$. In some examples, the sample gaseous substance comprises $H_2S$ and Ammonia ($NH_3$), and the at least one substance comprises $H_2S$. In some examples, the filtering element comprises $Pb(CH_3COO)_2$, $Zn(NO_3)_2$, $Ni(NO_3)_2$, $Co(NO_3)_2$, $Fe(NO_3)_2$ or $Mn(NO_3)_2$. In some examples, the filtering element and the target substance are associated with a solubility product constant that satisfies one or more target parameters.

In some examples, a method is provided. The method may comprise: receiving, by a controller component, a first concentration level indication associated with a first portion of a sample gaseous substance from a first sensing electrode; receiving, by the controller component, a second concentration level indication associated with a second portion of the sample gaseous substance from a second sensing electrode that is operatively coupled to a filtering element; and determining, by the controller component, a target substance concentration level indication based at least in part on the first concentration level indication and the second concentration level indication. In some examples, the filtering element is configured to absorb at least one substance from the sample gaseous substance. In some examples, the controller component is further configured to provide the target substance concentration level indication for display. In some examples, the first sensing electrode and the second sensing electrode are in a coplanar arrangement with respect to one another. In some examples, the filtering element is disposed above the first sensing electrode. In some examples, the sample gaseous substance comprises $H_2S$ and Methanethiol $CH_3SH$, the at least one substance comprises $H_2S$. In some examples, the first concentration level indication is associated with a concentration of $H_2S$ and $CH_3SH$, and wherein the second concentration level indication is associated with a concentration of $CH_3SH$. In some examples, the sample gaseous substance comprises $H_2S$ and $NH_3$, and the at least one substance comprises $H_2S$. In some examples, the filtering element comprises $Pb(CH_3COO)_2$, $Zn(NO_3)_2$, $Ni(NO_3)_2$, $Co(NO_3)_2$, $Fe(NO_3)_2$ or $Mn(NO_3)_2$. In some examples, the filtering element and the target substance are associated with a solubility product constant that satisfies one or more target parameters.

Referring now to FIG. 1, an example schematic diagram depicting a side section view of at least a portion of a sensing component 100 in accordance with some embodiments of the present disclosure is provided. In various embodiments, the sensing component 100 may be a portion of a gas detecting apparatus such as a electrochemical sensor. In various examples, the sensing component 100 may be at least partially disposed in a housing defining a cavity or reservoir configured to contain an electrolyte solution. The example electrolyte may comprise an aqueous acidic electrolyte such as sulfuric acid, phosphoric acid, or a neutral ionic solution such as a salt solution (e.g., a lithium salt such as lithium chloride), combinations thereof, and/or the like. In some embodiments, the electrolyte may be in the form of a solid polymer electrolyte which comprises an ionic exchange membrane. In some embodiments, the electrolyte can be in the form of a free liquid, disposed in a matrix or slurry such as glass fibers, or disposed in the form of a semi-solid or solid gel.

As depicted in FIG. 1, the sensing component 100 comprises a plurality of elements. In particular, as shown, the sensing component 100 comprises a filtering element 103, a first sensing electrode 105, a second sensing electrode 107, a reference electrode 109 and a counter electrode 111 disposed within a cavity defined by the housing of the sensing component 100. In various examples, the housing may comprise a polymeric material, a metal, or a ceramic. In some examples, the housing may comprise acrylonitrile butadiene styrene (ABS), polyphenylene oxide (PPO), polystyrene (PS), polypropylene (PP), polyethylene (PE) (e.g., high density polyethylene (HDPE)), polyphenylene ether (PPE), combinations thereof, and/or the like.

In particular, the example sensing component 100 may be configured to detect and/or measure a concentration of a target gaseous substance in a sample gaseous substance (e.g., air sample). In various examples, the example sensing component 100 may be configured to detect and/or measure a concentration of a particular gaseous substance. By way of example, the example sensing component 100 may be configured to detect $H_2S$ or $CH_3SH$. As the sample gaseous substance 102 enters the sensing component 100 to be incident on the first sensing electrode 105 and the second sensing electrode 107, an electrochemical reaction occurs. In various examples, the electrochemical reaction may be an oxidation or reduction depending on the type of sample gaseous substance 102. For example, carbon monoxide may be oxidized to carbon dioxide, or oxygen may be reduced to water. An oxidation reaction results in the flow of electrons from the first sensing electrode 105 and the second sensing electrode 107 to the counter electrode 111. Conversely a reduction reaction results in flow of electrons from the counter electrode 111 to the first sensing electrode 105 and the second sensing electrode 107. The flow of electrons creates an electric current that is proportional to the concentration of a target substance in the sample gaseous substance 102. As noted above, the sensing component 100 may be a portion of a gas detecting apparatus (e.g., electrochemical sensor). The gas detecting apparatus may be configured to further detect and amplify the current generated by the sensing component 100. Additionally, a controller component of the gas detecting apparatus may be configured to interpret characteristics of the current generated by the sensing component such that a concentration of the target substance can be provided (e.g., in percent volume, parts per million (PPM), parts per billion (PPB), or the like). Additionally, the controller component may calculate and store a detected concentration level in memory.

As depicted in FIG. 1, the sensing component 100 comprises a first sensing electrode 105 (e.g., auxiliary electrode) and a second sensing electrode 107. As illustrated, the first sensing electrode 105 and the second sensing electrode 107 are disposed below a top surface of the example portion of a sensing component 100. As illustrated in FIG. 1, a sample gaseous substance 102 (such as an air sample) may flow into an aperture 104 through at least a portion of the example sensing component 100 such that the sample gaseous substance (e.g., air sample) flows through the sensing component 100 and makes contact with the first sensing electrode 105 and the second sensing electrode 107. As depicted, the aperture 104 defines an opening on a top surface of the sensing component 100. However, the aperture 104 may define an opening on any other surface of the sensing component 100. By way of example, the aperture 104 may have a diameter between 150 μm and 5 mm. In some embodiments, the sensing component 100 may comprise a plurality of apertures through which a sample gaseous substance 102 may enter and exit the sensing component 100 (e.g., a gas inlet and a gas outlet). In some embodiments, the sample gaseous substance 102 may exit the sensing component 100 through the aperture 104. In some embodiments, the aperture 104 may comprise a diffusion barrier to restrict and/or direct the flow of gaseous substances (e.g., to the first sensing electrode 105 and the second sensing electrode 107). The example diffusion barrier can be created by forming the aperture 104 as a capillary and/or a film or membrane can be used to control the mass flow rate through the aperture 104.

In various embodiments, the cavity defined by the sensing component 100 which contains the above-noted elements (i.e., the filtering element 103, the first sensing electrode 105, the second sensing electrode 107, the reference electrode 109 and the counter electrode 111) may comprise an electrolyte (e.g., a liquid electrolyte). The first sensing electrode 105, the second sensing electrode 107, the reference electrode 109 and the counter electrode 111 may be in electrical contact with one another via the electrolyte. In some embodiments, the cavity of the sensing component 100 comprises one or more porous separators and/or porous structures that operate to retain the electrolyte in contact with the first sensing electrode 105, the second sensing electrode 107, the reference electrode 109 and the counter electrode 111. In some embodiments, the one or more porous separators and/or porous structures may comprise a nonwoven porous material (e.g., a porous felt member), a woven porous material, a porous polymer (e.g., an open cell foam, a solid porous plastic) or the like. In general, the one or more porous separators and/or porous structures may be chemically inert with respect to the electrolyte and the first sensing electrode 105, the second sensing electrode 107, the reference electrode 109 and the counter electrode 111. In some embodiments, the one or more porous separators and/or porous structures may comprise various materials including, but not limited to, glass (e.g., a glass mat), polymer (plastic discs), ceramics, or the like. The porous separators and/or porous structures may operate as wicks for the retention and transportation of the electrolyte within the cavity of the sensing component 100 while providing electrical insulation to prevent shorting due to direct contact between any two electrodes. In some embodiments, the porous separators and/or porous structures may extend into a reservoir disposed beneath the arrangement of the first sensing electrode 105, the second sensing electrode 107, the reference electrode 109 and the counter electrode 111 and may provide the electrolyte a path to the first sensing electrode 105, the second sensing electrode 107, the reference electrode 109 and the counter electrode 111. By way of example, a first porous separator/structure may be disposed between the reference electrode 109 and the counter electrode 111 and a second porous separator/structure may be disposed between the reference electrode 109 and the first sensing electrode 105 and the second sensing electrode 107.

As depicted in FIG. 1, the first sensing electrode 105 and the second sensing electrode 107 are disposed coplanar with respect to one another. As further depicted, the reference electrode 109 is disposed beneath the first sensing electrode 105 and the second sensing electrode 107 and the counter electrode is disposed beneath the reference electrode 109. As depicted in FIG. 1, each of the first sensing electrode 105, the second sensing electrode 107, the reference electrode 109 and the counter electrode 111 comprises a gas permeable substrate or membrane. When a sample gaseous substance 102 (e.g., air sample) enters the cavity of the sensing component 100 through the aperture 104 on the upper surface of the housing, the sample gaseous substance 102 may cause a reaction at the interface between the first sensing electrode 105/the second sensing electrode 107 and the electrolyte. An electrical current and/or potential can be developed between the electrodes to provide an indication of the concentration of a target substance. The reference electrode 109 may provide a reference for the detected current and potential between the first sensing electrode 105/the second sensing electrode 107 and the counter electrode 111. The reference electrode 109 may also be configured to provide a reference for the potential of the first sensing electrode 105/the second sensing electrode 107 relative to a standard reference electrode, e.g., a reversible hydrogen electrode.

As depicted in FIG. 1, the sensing component 100 comprises a filtering element 103 operatively coupled to the first sensing electrode 105. As shown, the filtering element 103 is disposed at least partially above the first sensing electrode 105. In some examples, at least a portion of the filtering element 103 may be in direct contact with the first sensing electrode 105. In various embodiments, the filtering element 103 is operatively coupled to the first sensing electrode 105 so as to filter out (e.g., absorb, react with, or the like) a target substance. In some embodiments, the first sensing electrode 105 and the second sensing electrode 107 may be similar or identical to one another. While FIG. 1 provides an example of a filtering element 103 that is operatively coupled to the first sensing electrode 105, in some embodiments, the filtering element 103 may be coupled to the second sensing electrode 105. It should be understood that in various examples, the filtering element 103 can be coupled to any one of a plurality of sensing electrodes (e.g., three sensing electrodes, four sensing electrodes, or the like)

In some examples, the sample gaseous substance may comprise a plurality of substances such as, in some examples, a mixture of $H_2S$ and $CH_3SH$. In some examples, the plurality of gases may comprise a mixture of $H_2S$ and $NH_3$, where $H_2S$ is the target substance. In the example of a mixture of $H_2S$ and $CH_3SH$ being present in a sample gaseous substance, the filtering element 103 may be configured to selectively and fully absorb $H_2S$ leaving only the $CH_3SH$ to penetrate through the filtering element 103 and react with the first sensing electrode 105 disposed thereneath. In the above example, the filtering element 103 may be or comprise a chemical filter that is configured to absorb a target gaseous substance (e.g., a lead acetate filter, i.e., $Pb(CH_3COO)_2$, may be utilized to absorb $H_2S$). The below formula describes an example of an oxidizing reaction between $H_2S$ and $Pb(CH_3COO)_2$.

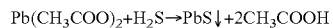

$$Pb(CH_3COO)_2 + H_2S \rightarrow PbS\downarrow + 2CH_3COOH$$

In some examples, the filtering element 103 and the target substance (e.g., $H_2S$) are associated with a solubility product constant (Ksp) that satisfies one or more target parameters. The term Ksp may refer to an equilibrium constant for a first substance reacting with another substance and may be utilized to evaluate the combination affinity between two reactants. A reaction between two reactants may be associated with a particular Ksp, where a small Ksp is indicative of a stronger combination affinity between two reactants. In the above example, when $Pb(CH_3COO)_2$ reacts with $H_2S$, the key reaction is $Pb^{2+} + S^{2-} \rightarrow PbS$. Accordingly, the reaction between $Pb^{2+}$ and $S^{2-}$ will reach an equilibrium very quickly relative to other candidate filtering elements as evidenced by a small Ksp. In contrast, the $CH_3SH$ will not be absorbed by the filtering element 103 in accordance with the below formula:

$$Pb(CH_3COO)_2 + CH_3SH \rightarrow \text{No reaction}$$

Thus, in some embodiments, $Pb(CH_3COO)_2$ can effectively bind to inorganic sulfide in $H_2S$ molecules but is negligibly weak with respect to binding with organic sulfide in $CH_3SH$.

In some examples, the filtering element 103 may be or comprise $Ag_2SO4$ which can also be utilized to $Ag_2SO4$ absorb sulfide containing gases (e.g., $H_2S$). By way of example, the Ksp associated with PbS is larger relative to the Ksp associated with $Ag_2S$. Accordingly, in some examples, $Ag^+$ may also absorb sulfide containing gases with ease relative to certain other candidate filtering elements. However, with respect to candidate filtering elements for detecting $H_2S$ and $CH_3SH$, Ag+ can absorb both $H_2S$ and $CH_3SH$ and therefore will not generate any signal over a sensing electrode. Thus, an $Ag_2S$ filter is not workable for accurate detection of $H_2S$ and $CH_3SH$.

Consequently, the appropriate filtering element for a particular target gaseous substance may be based at least in part on a Ksp that satisfies certain parameters (e.g., a precipitation free energy range associated with a target gaseous substance). Table 1 below provides a plurality of candidate filtering elements for absorbing $H_2S$ and $CH_3SH$ based at least in part on a Ksp that satisfies and/or falls below a particular threshold.

TABLE 1

Candidate filtering elements for absorbing $H_2S$ from a mixture of $H_2S$ and $CH_3SH$.

| Workable Filtering Element Candidates | Ksp |
|---|---|
| $Pb(CH_3COO)_2$ | Ksp (PbS) = 8.0 * $10^{-28}$ |
| $Zn(NO_3)_2$ | Ksp (ZnS) = 2.9 * $10^{-25}$ |
| $Ni(NO_3)_2$ | Ksp (NiS) = 1.1 * $10^{-21}$ |
| $Co(NO_3)_2$ | Ksp (CoS) = 4.0 * $10^{-21}$ |

TABLE 1-continued

Candidate filtering elements for absorbing $H_2S$ from a mixture of $H_2S$ and $CH_3SH$.

| Workable Filtering Element Candidates | Ksp |
|---|---|
| $Fe(NO_3)_2$ | Ksp (FeS) = 6.3 * $10^{-18}$ |
| $Mn(NO_3)_2$ | Ksp (MnS) = 2.5 * $10^{-13}$ |

Returning to FIG. 1, as depicted, in contrast with the first sensing electrode 105, the second sensing electrode 107 does not comprise a filtering element and therefore both the $H_2S$ and $CH_3SH$ in the sample gaseous substance will pass through the second sensing electrode 107 thus providing a combined signal corresponding to the presence and/or concentration of both $H_2S$ and $CH_3SH$. Thus, in the above example, an accurate measurement of a concentration of $H_2S$ can be determined by deducting the output of the first sensing electrode 105 (e.g., corresponding with a $CH_3SH$ signal) from the output of the second sensing electrode 107 (e.g., corresponding with a $H_2S$ and $CH_3SH$ signal) in accordance with the below formula:

Second sensing electrode signal−First sensing electrode signal=target substance signal By way of example, using the above formula, the output of the second sensing electrode comprises an $CH_3SH$ signal and $H_2S$ signal, the output of the first sensing electrode 105 comprises a $CH_3SH$ signal and the target substance signal is a pure $H_2S$ signal. Utilizing the above techniques, the complexity of the algorithm utilized by a gas detecting apparatus in order to accurately detect and/measure one or more target substances in a sample gaseous substance is significantly reduced.

While FIG. 1 provides an example of a sensing component 100, it is noted that the scope of the present disclosure is not limited to the example shown in FIG. 1. In some examples, an example sensing component 100 may comprise one or more additional and/or alternative elements, and/or may be structured/positioned differently than those illustrated in FIG. 1. For example, a sensing component 100 in accordance with the present disclosure may comprise more than two sensing electrodes.

Figure 2A:
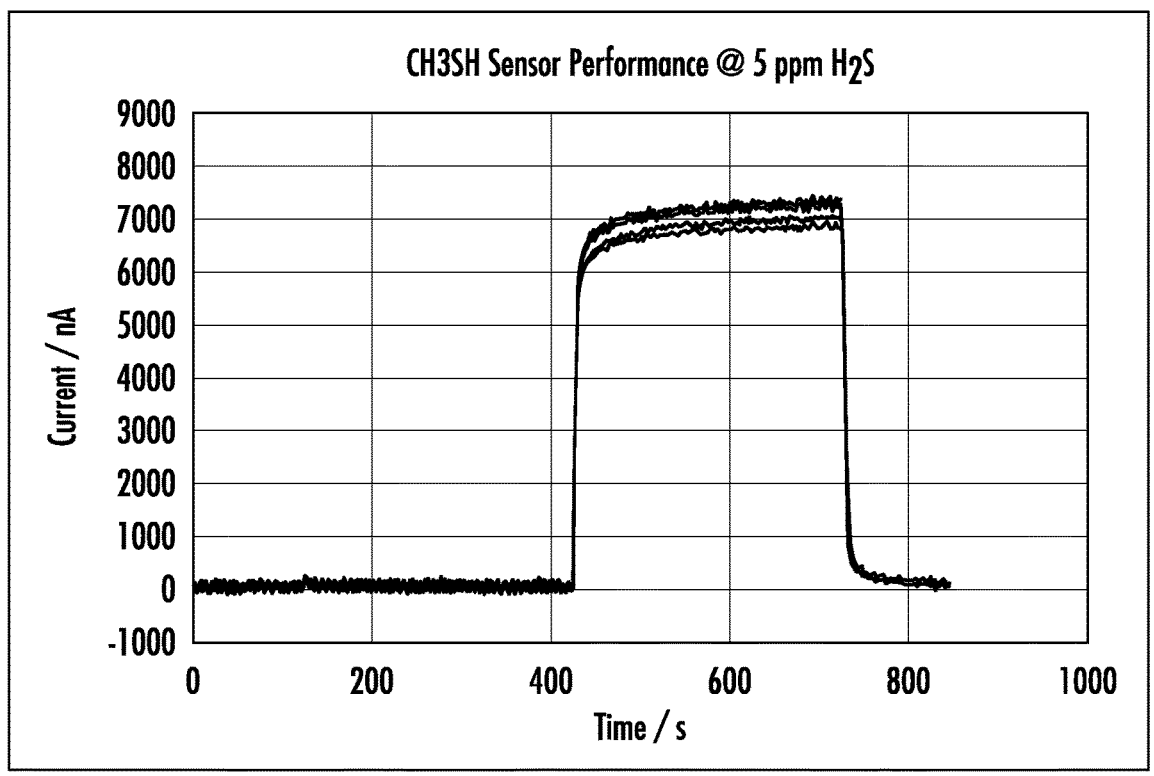
FIG. 2A-FIG. 2B illustrate graphs depicting example measurements in accordance with various embodiments of the present disclosure.
Figure 2B:
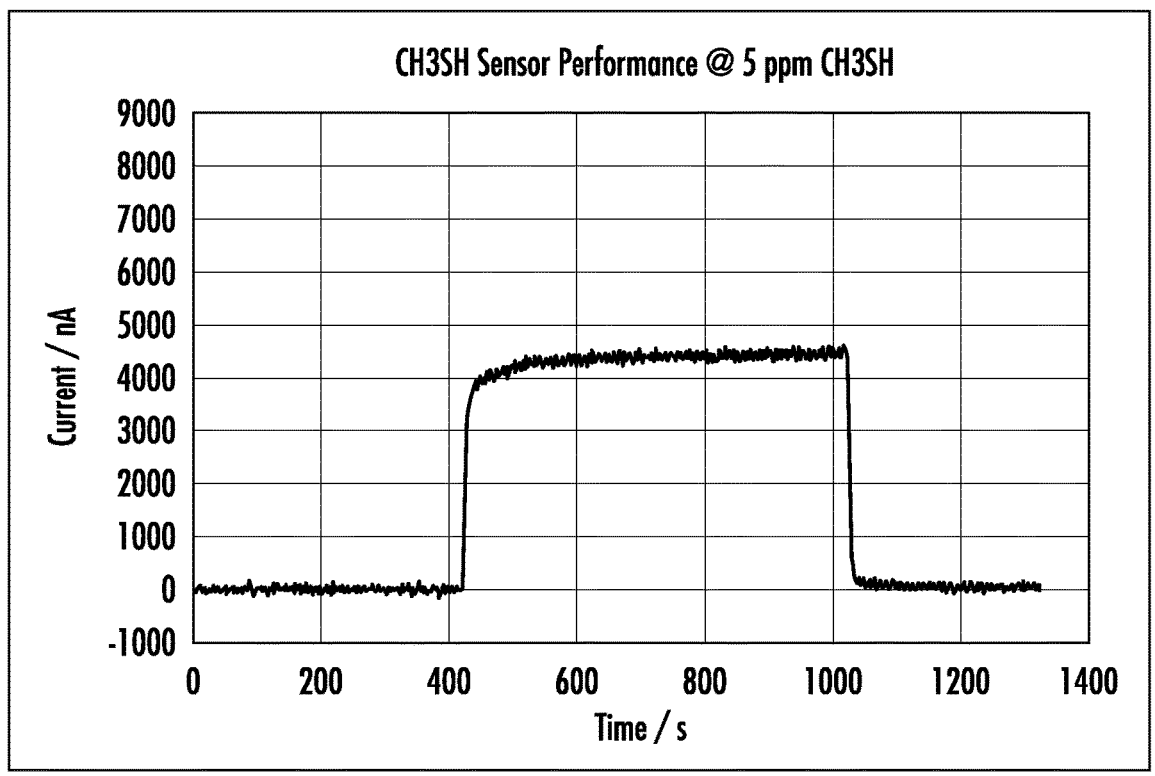

Referring now to FIG. 2A and FIG. 2B, example graphs 200A and 200B depicting example measurements by a conventional sensing electrode are provided.

As depicted in FIG. 2A, the x-axis represents a plurality of instances in time. As depicted, the y-axis represents a detected current signal by a conventional sensing electrode measured in nanoamperes (nA) corresponding with a concentration of a gaseous substance (5 ppm of $H_2S$). As illustrated in FIG. 2A, responsive to a sample gaseous substance comprising $H_2S$, the conventional sensing electrode detects a current signal (as depicted, approximately between 400 and 800 along the x-axis).

As depicted in FIG. 2B, the x-axis represents a plurality of instances in time. As depicted, the y-axis represents a detected current signal by a conventional sensing electrode measured in nA corresponding with a concentration of a gaseous substance (5 ppm of $CH_3SH$). As illustrated in FIG. 2B, responsive to a sample gaseous substance comprising $CH_3SH$, the conventional sensing electrode detects a current signal (as depicted, approximately between 400 and 1000 along the x-axis).

Accordingly, FIG. 2A and FIG. 2B demonstrate that the conventional sensing electrode will detect both $H_2S$ and $CH_3SH$, respectively. Thus it should be understood that the conventional sensing electrode may generate inaccurate measurements with respect to $H_2S$ and $CH_3SH$ when an example gaseous substance comprises both $H_2S$ and $CH_3SH$ which in turn affects the accuracy of measurements that are outputted by an example gas detecting apparatus (e.g., electrochemical detector) associated therewith.

Figure 3A:
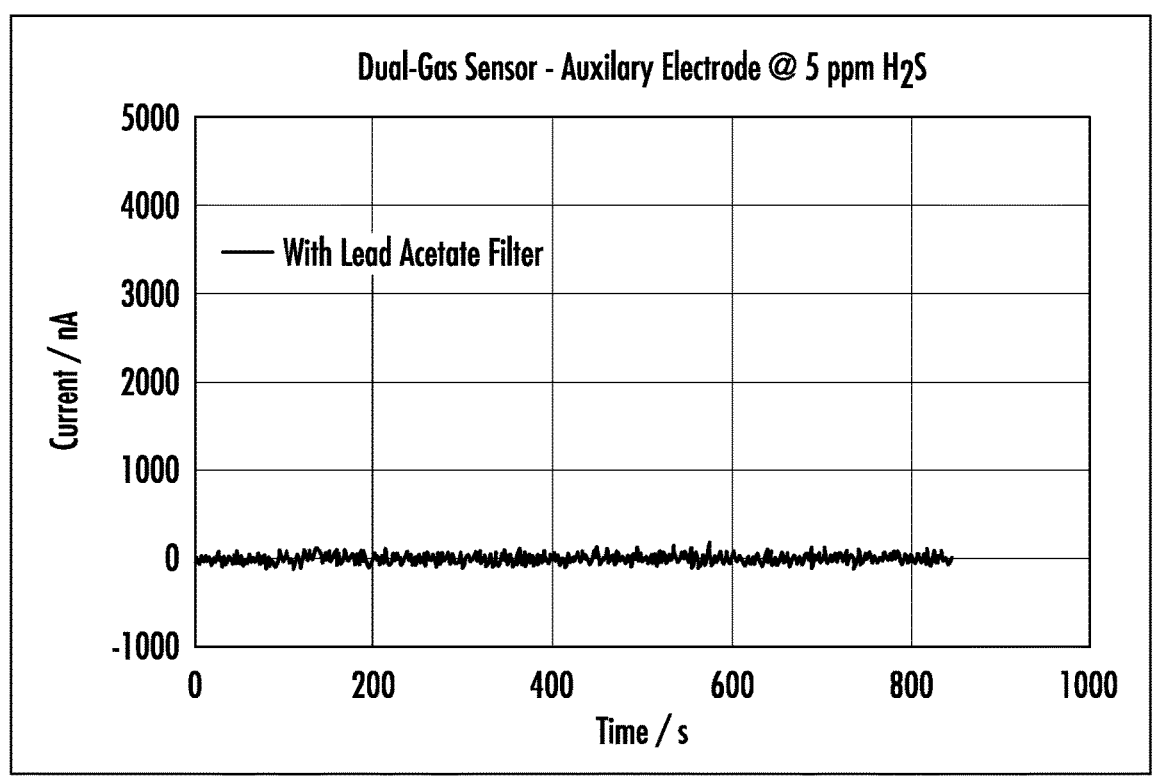
FIG. 3A-FIG. 3B illustrate graphs depicting example measurements in accordance with various embodiments of the present disclosure.
Figure 3B:
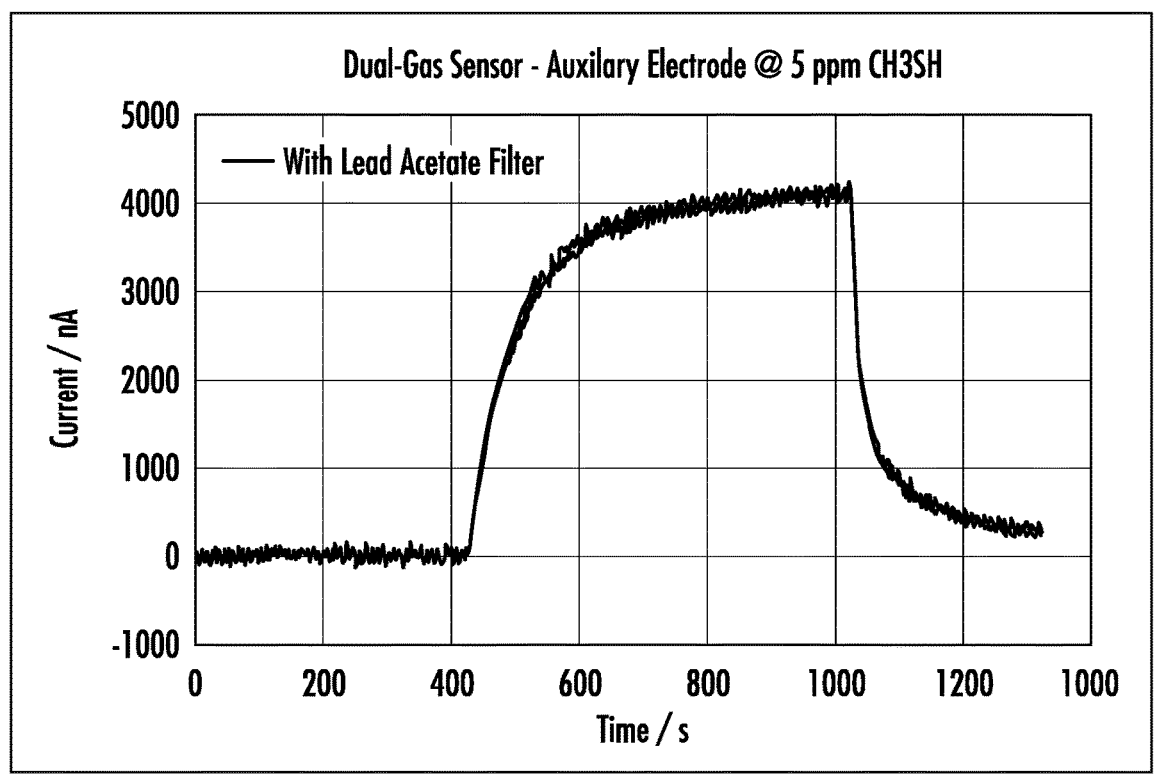

Referring now to FIG. 3A and FIG. 3B, example graphs 300A and 300B depicting example measurements by a sensing electrode operatively coupled to filtering element that is configured to absorb a target gaseous substance (i.e., $H_2S$) in accordance with various embodiments of the present disclosure are provided. The sensing electrode may be similar or identical to the first sensing electrode 105 that is operatively coupled to the filtering element 103 discussed above in relation to FIG. 1. The sensing electrode may be a portion of a sensing component and/or gas detecting apparatus (e.g., electrochemical detector).

As depicted in FIG. 3A, the x-axis represents a plurality of instances in time. As depicted, the y-axis represents a detected current signal by the sensing electrode measured in nA corresponding with a concentration of a gaseous substance (5 ppm of $H_2S$). As illustrated in FIG. 3A, responsive to a sample gaseous substance comprising $H_2S$, the sensing electrode (e.g., the filtering element) is able to fully absorb the $H_2S$ such that no current signal corresponding with/attributable to the presence of $H_2S$ is detected.

As depicted in FIG. 3B, the x-axis represents a plurality of instances in time. As depicted, the y-axis represents a detected current signal by the sensing electrode measured in nA corresponding with a concentration of a gaseous substance (5 ppm of $CH_3SH$). As illustrated in FIG. 3B, responsive to a sample gaseous substance comprising $CH_3SH$, the sensing electrode detects a current signal (as depicted, approximately between 400 and 1000 along the x-axis).

Accordingly, FIG. 3A and FIG. 3B demonstrate that the sensing electrode operatively coupled to a filtering element will detect $CH_3SH$, but will not detect $H_2S$ which will be absorbed by the filtering element. Thus it should be understood that a sensing component incorporating the sensing electrode in accordance with the present disclosure will generate accurate measurements with respect to $H_2S$ and/or $CH_3SH$, when an example gaseous substance comprises both $H_2S$ and $CH_3SH$ which in turn improves the accuracy of measurements that are outputted by an example gas detecting apparatus (e.g., electrochemical detector) associated therewith.

Figure 4:
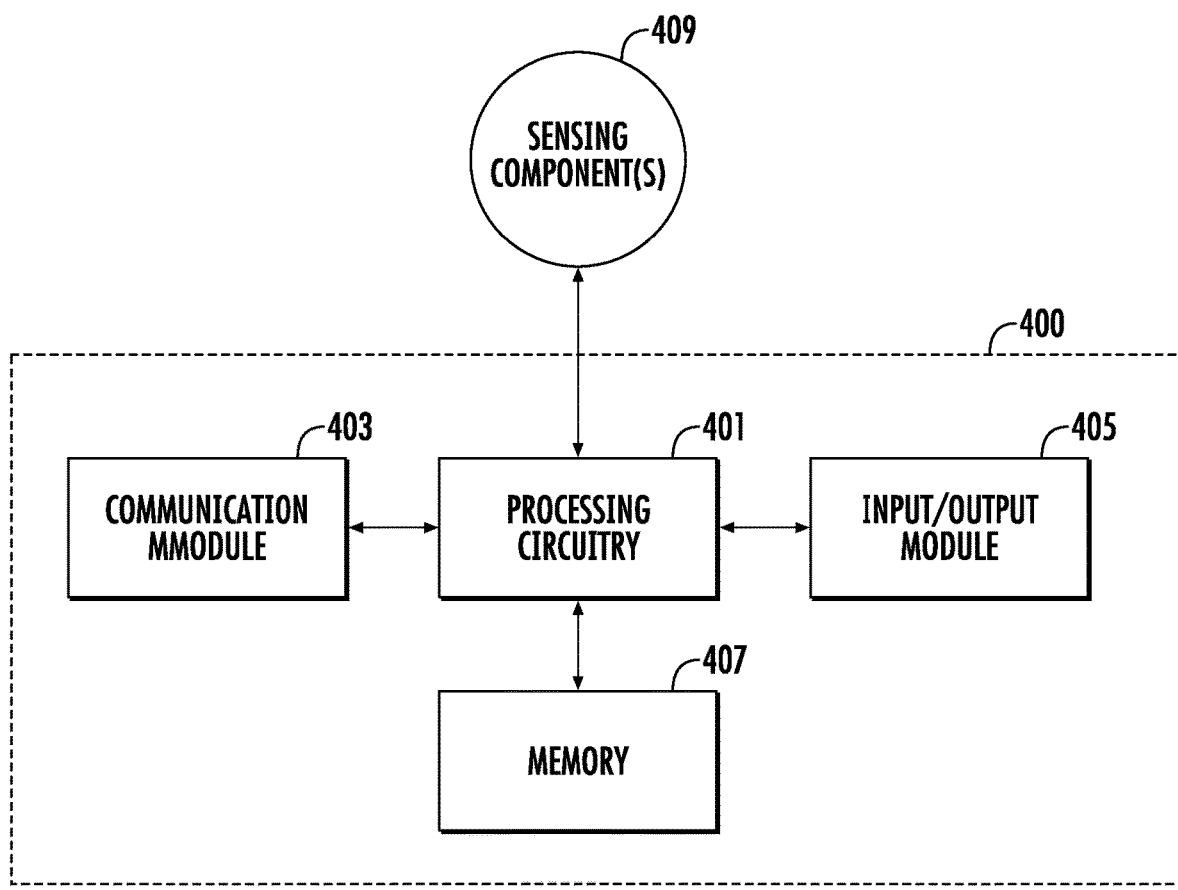
FIG. 4 illustrates an example controller component in electronic communication with other element(s)/component(s) of an example gas detecting apparatus in accordance with various embodiments of the present disclosure.

Referring now to FIG. 4, a schematic diagram depicting an example controller component 400 of an example gas detecting apparatus in electronic communication with various other components in accordance with various embodiments of the present disclosure. As shown, the controller component 400 comprises processing circuitry 401, a communication module 403, input/output module 405, a memory 407 and/or other components configured to perform various operations, procedures, functions or the like described herein.

As shown, the controller component 400 (such as the processing circuitry 401, communication module 403, input/output module 405 and memory 407) is electrically coupled to and/or in electronic communication with a sensing component 409 (e.g., comprising a gas detecting element). The sensing component 409 may be similar to the sensing component 100 described above in connection with FIG. 1. As depicted, the sensing component 409 may exchange (e.g., transmit and receive) data with the processing circuitry 401 of the controller component 400.

The processing circuitry 401 may be implemented as, for example, various devices comprising one or a plurality of microprocessors with accompanying digital signal processors; one or a plurality of processors without accompanying digital signal processors; one or a plurality of coprocessors; one or a plurality of multi-core processors; one or a plurality of controllers; processing circuits; one or a plurality of computers; and various other processing elements (including integrated circuits, such as ASICs or FPGAs, or a certain combination thereof). In some embodiments, the processing circuitry 401 may comprise one or more processors. In one exemplary embodiment, the processing circuitry 401 is configured to execute instructions stored in the memory 407 or otherwise accessible by the processing circuitry 401. When executed by the processing circuitry 401, these instructions may enable the controller component 400 to execute one or a plurality of the functions as described herein. No matter whether it is configured by hardware, firmware/software methods, or a combination thereof, the processing circuitry 401 may comprise entities capable of executing operations according to the embodiments of the present invention when correspondingly configured. Therefore, for example, when the processing circuitry 401 is implemented as an ASIC, an FPGA, or the like, the processing circuitry 401 may comprise specially configured hardware for implementing one or a plurality of operations described herein. Alternatively, as another example, when the processing circuitry 401 is implemented as an actuator of instructions (such as those that may be stored in the memory 407), the instructions may specifically configure the processing circuitry 401 to execute one or a plurality of algorithms and operations described herein, such as those discussed with reference to FIG. 5.

The memory 407 may comprise, for example, a volatile memory, a non-volatile memory, or a certain combination thereof. Although illustrated as a single memory in FIG. 4, the memory 407 may comprise a plurality of memory components. In various embodiments, the memory 407 may comprise, for example, a hard disk drive, a random access memory, a cache memory, a flash memory, a Compact Disc Read-Only Memory (CD-ROM), a Digital Versatile Disk Read-Only Memory (DVD-ROM), an optical disk, a circuit configured to store information, or a certain combination thereof. The memory 407 may be configured to store information, data, application programs, instructions, and etc., so that the controller component 400 can execute various functions according to the embodiments of the present disclosure. For example, in at least some embodiments, the memory 407 is configured to cache input data for processing by the processing circuitry 401. Additionally or alternatively, in at least some embodiments, the memory 407 is configured to store program instructions for execution by the processing circuitry 401. The memory 407 may store information in the form of static and/or dynamic information. When the functions are executed, the stored information may be stored and/or used by the controller component 400.

The communication module 403 may be implemented as any apparatus included in a circuit, hardware, a computer program product or a combination thereof, which is configured to receive and/or transmit data from/to another component or apparatus. The computer program product comprises computer-readable program instructions stored on a computer-readable medium (for example, the memory 407) and executed by a controller component 400 (for example, the processing circuitry 401). In some embodiments, the communication module 403 (as with other components discussed herein) may be at least partially implemented as the processing circuitry 401 or otherwise controlled by the processing circuitry 401. In this regard, the communication module 403 may communicate with the processing circuitry 401, for example, through a bus. The communication module 403 may comprise, for example, antennas, transmitters, receivers, transceivers, network interface cards and/or supporting hardware and/or firmware/software, and is used for establishing communication with another apparatus. The communication module 403 may be configured to receive and/or transmit any data that may be stored by the memory 407 by using any protocol that can be used for communication between apparatuses. The communication module 403 may additionally or alternatively communicate with the memory 407, the input/output module 405 and/or any other component of the controller component 400, for example, through a bus.

In some embodiments, the controller component 400 may comprise an input/output module 405. The input/output module 405 may communicate with the processing circuitry 401 to receive instructions input by the user and/or to provide audible, visual, mechanical or other outputs to the user. Therefore, the input/output module 405 may comprise supporting devices, such as a keyboard, a mouse, a display, a touch screen display, and/or other input/output mechanisms. Alternatively, at least some aspects of the input/output module 405 may be implemented on a device used by the user to communicate with the controller component 400. The input/output module 405 may communicate with the memory 407, the communication module 403 and/or any other component, for example, through a bus. One or a plurality of input/output modules and/or other components may be included in the controller component 400.

For example, the sensing component 409 may be similar to sensing component 100 described above with regard to FIG. 1. For example, sensing component 409 may generate measurements indicating a concentration level of one or more target gaseous substance in a sample gaseous substance and transmit a concentration level indication to the processing circuitry 401.

Figure 5:
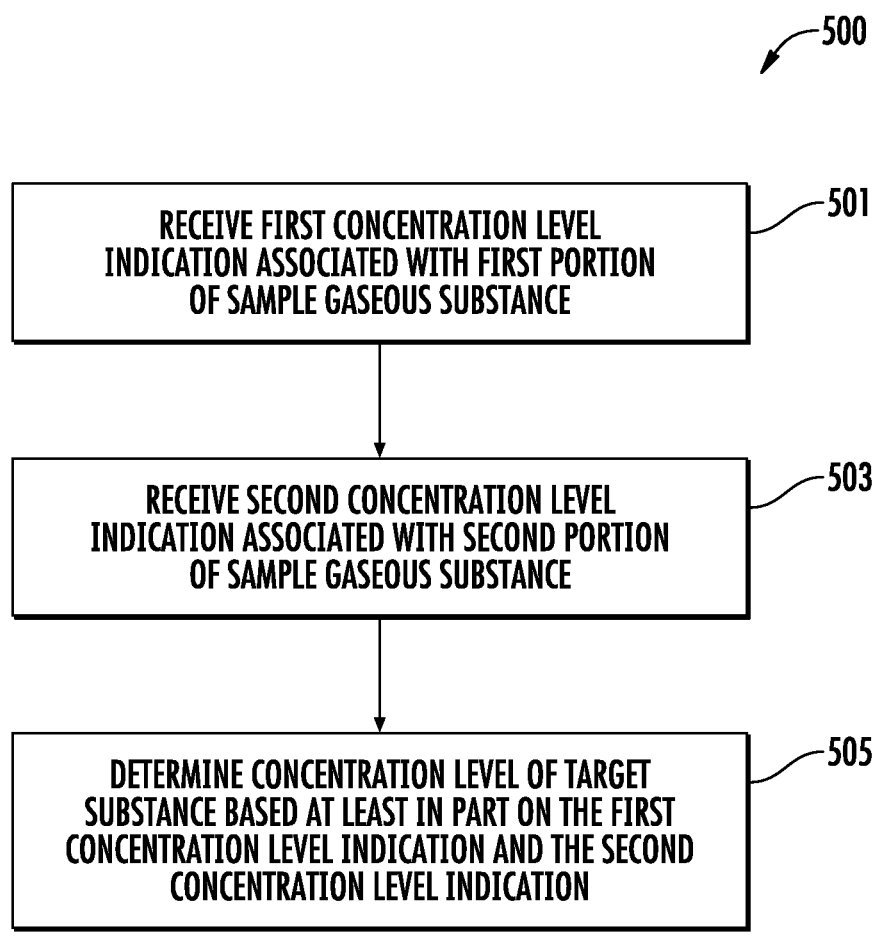
FIG. 5 is a flowchart diagram illustrating example operations in accordance with various embodiments of the present disclosure.

Referring now to FIG. 5, a flowchart diagram illustrating an example method 500 in accordance with various embodiments of the present disclosure is provided.

In some examples, the method 500 may be performed by a processing circuitry (for example, but not limited to, an application-specific integrated circuit (ASIC), a central processing unit (CPU)). In some examples, the processing circuitry may be electrically coupled to and/or in electronic communication with other circuitries of the example apparatus, such as, but not limited to, a sensing component, a memory (such as, for example, random access memory (RAM) for storing computer program instructions), and/or a display circuitry (for rendering readings on a display).

In some examples, one or more of the procedures described in FIG. 5 may be embodied by computer program instructions, which may be stored by a memory (such as a non-transitory memory) of a system employing an embodiment of the present disclosure and executed by a processing circuitry (such as a processor) of the system. These computer program instructions may direct the system to function in a particular manner, such that the instructions stored in the memory circuitry produce an article of manufacture, the execution of which implements the function specified in the flow diagram step/operation(s). Further, the system may comprise one or more other circuitries. Various circuitries of the system may be electronically coupled between and/or among each other to transmit and/or receive energy, data and/or information.

In some examples, embodiments may take the form of a computer program product on a non-transitory computer-readable storage medium storing computer-readable program instruction (e.g., computer software). Any suitable computer-readable storage medium may be utilized, including non-transitory hard disks, CD-ROMs, flash memory, optical storage devices, or magnetic storage devices.

The example method 500 begins at step/operation 501. At step/operation 501, a processing circuitry (such as, but not limited to, the processing circuitry 401 of the controller component 400 illustrated in connection with FIG. 4, discussed above) receives a first concentration level indication associated with a sample gaseous substance (e.g., a first portion of a sample gaseous substance). In some embodiments, a sensing component (such as, but not limited to, the sensing component 100 illustrated in connection with FIG. 1) may transmit a first concentration level indication associated with a first portion of a sample gaseous substance to the processing circuitry. The first concentration level indication may be associated with a first sensing electrode that is configured to detect a plurality of substances (e.g., $H_2S$ and $CH_3SH$) generated in response to the sample gaseous substance making contact with the first sensing electrode as the sample gaseous substance is dispersed within/flows into and through the sensing component. In various examples, concentration of the target gaseous substance(s) may be measured in parts-per-million (ppm), parts-per-billion (ppb), milligrams-per-cubic-meter (mg/m3), or the like. In some examples, the example sensing component may periodically provide a concentration level indication. In some examples, the optical component may provide a concentration level indication in response to a request (e.g., in response to receiving a control signal or indication from the processing circuitry).

Subsequent to step/operation 501, the example method 500 proceeds to step/operation 503. At step/operation 503, the processing circuitry receives a second concentration level indication associated with the sample gaseous substance (e.g., a second portion of the sample gaseous substance). The sensing component may transmit a second concentration level indication associated with a second portion of the sample gaseous substance to the processing circuitry. The second concentration level indication may be associated with a second electrode that is operatively coupled to a filtering element configured to absorb/filter out a target substance from the sample gaseous substance (e.g., $H_2S$). For example, if the filtering element is configured to absorb $H_2S$ from a sample gaseous substance that comprises $H_2S$ and $CH_3SH$, then the second concentration level indication may be associated with only $CH_3SH$ as a result of a portion of sample gaseous substance without $H_2S$ making contact with the second sensing electrode as the sample gaseous substance is dispersed within/flows into and through the filtering element prior to reaching the second sensing electrode.

Subsequent to step/operation 503, the method 500 proceeds to step/operation 505. At step/operation 505, the processing circuitry determines the concentration level of a target substance based at least in part on the first concentration level indication and the second concentration level indication. For example, the processing circuitry may determine the concentration level of the target substance by deducting the second concentration level indication from the first concentration level indication. For instance, if the sample gaseous substance comprises $H_2S$ and $CH_3SH$, the first concentration level indication is associated with $H_2S$ and $CH_3SH$ and the second concentration level indication is associated with only $CH_3SH$, the processing circuitry can determine the concentration level of $H_2S$ (i.e., the target substance) by deducting the first concentration level indication from the second concentration level indication. The processing circuitry may then provide a target substance concentration level indication and/or a warning indication for display. For example, the processing circuitry may provide or generate a target substance concentration level indication, warning indication, alert, and/or the like for presentation. In some examples, the target substance concentration level indication and/or warning indication may be provided for display via a display or user interface of an example gas detecting apparatus (e.g., electrochemical detector). Additionally and/or alternatively, the target substance concentration level indication and/or warning indication may be provided for display via another user computing device in electronic communication with the example gas detecting apparatus. Accordingly, using the techniques described herein, the accuracy of measurements and corresponding warning indications/alerts provided by a gas detecting apparatus may be significantly improved without utilizing complex algorithms and electronics.

Many modifications and other embodiments of the present disclosure set forth herein will come to mind to one skilled in the art to which these embodiments pertain having the benefit of the teachings presented in the foregoing descriptions and the associated drawings. Therefore, it is to be understood that the disclosure are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

The invention claimed is:

1. A gas detecting apparatus comprising a sensing component, the sensing component comprising:
   a first sensing electrode configured to generate a first concentration level indication associated with a first portion of a sample gaseous substance disposed within the sensing component; and
   a second sensing electrode operatively coupled to a filtering element configured to absorb at least one substance from the sample gaseous substance, wherein the second sensing electrode is configured to generate a second concentration level indication associated with a second portion of the sample gaseous substance, wherein the filtering element comprises $Pb(CH_3COO)_2$, $Zn(NO_3)_2$, $Ni(NO_3)_2$, $Co(NO_3)_2$, $Fe(NO_3)_2$ or $Mn(NO_3)_2$.

2. The gas detecting apparatus of claim 1, further comprising a controller component in electronic communication with the sensing component.

3. The gas detecting apparatus of claim 2, wherein the controller component is configured to:
receive the first concentration level indication and the second concentration level indication; and
determine a target substance concentration level based at least in part on the first concentration level indication and the second concentration level indication.

4. The gas detecting apparatus of claim 1, wherein the first sensing electrode and the second sensing electrode are in a coplanar arrangement with respect to one another.

5. The gas detecting apparatus of claim 1, wherein:
the sample gaseous substance comprises Hydrogen Sulfide ($H_2S$) and Methanethiol ($CH_3SH$), and the at least one substance comprises $H_2S$.

6. The gas detecting apparatus of claim 5, wherein:
the first concentration level indication is associated with a concentration of $H_2S$ and $CH_3SH$, and
the second concentration level indication is associated with a concentration of $CH_3SH$.

7. The gas detecting apparatus of claim 1, wherein:
the sample gaseous substance comprises $H_2S$ and Ammonia ($NH_3$), and the at least one substance comprises $H_2S$.

8. The gas detecting apparatus of claim 1, wherein the filtering element and the at least one substance are associated with a solubility product constant that satisfies one or more parameters.

9. A method comprising:
receiving, by a controller component, a first concentration level indication associated with a first portion of a sample gaseous substance from a first sensing electrode;
receiving, by the controller component, a second concentration level indication associated with a second portion of the sample gaseous substance from a second sensing electrode that is operatively coupled to a filtering element, wherein the filtering element comprises $Pb(CH_3COO)_2$, $Zn(NO_3)_2$, $Ni(NO_3)_2$, $Co(NO_3)_2$, $Fe(NO_3)_2$ or $Mn(NO_3)_2$; and
determining, by the controller component, a target substance concentration level indication based at least in part on the first concentration level indication and the second concentration level indication.

10. The method of claim 9, wherein the filtering element is configured to absorb at least one substance from the sample gaseous substance.

11. The method of claim 10, wherein:
the sample gaseous substance comprises Hydrogen Sulfide ($H_2S$) and Methanethiol ($CH_3SH$), and the at least one substance comprises $H_2S$.

12. The method of claim 11, wherein the first concentration level indication is associated with a concentration of $H_2S$ and $CH_3SH$, and wherein the second concentration level indication is associated with a concentration of $CH_3SH$.

13. The method of claim 10, wherein the sample gaseous substance comprises $H_2S$ and Ammonia ($NH_3$), and the at least one substance comprises $H_2S$.

14. The method of claim 10, wherein the filtering element and the at least one substance are associated with a solubility product constant that satisfies one or more parameters.

15. The method of claim 9, wherein the controller component is further configured to provide the target substance concentration level indication for display.

16. The method of claim 9, wherein the first sensing electrode and the second sensing electrode are in a coplanar arrangement with respect to one another.

\* \* \* \* \*